(12) United States Patent
Lutz

(10) Patent No.: US 6,297,285 B1
(45) Date of Patent: *Oct. 2, 2001

(54) DISINFECTING USE OF QUATERNARY AMMONIUM CARBONATES

(75) Inventor: Patrick J. Lutz, Easton, PA (US)

(73) Assignee: Lonza, Inc., Annadale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/592,311

(22) Filed: Jun. 13, 2000

Related U.S. Application Data

(63) Continuation of application No. 08/931,184, filed on Sep. 16, 1997, now Pat. No. 6,080,789, which is a continuation of application No. 08/352,899, filed on Dec. 9, 1994, now abandoned.

(51) Int. Cl.$^7$ .......................... A01N 33/12; A61L 21/18; A61L 2/18; B65B 55/18; C11D 9/50
(52) U.S. Cl. .................. 514/642; 514/553; 514/578; 504/157; 504/158; 422/28; 510/384
(58) Field of Search ..................... 504/158, 157; 424/405, 541, 642, 643; 422/1, 28; 514/642, 553, 578; 510/384

(56) References Cited

U.S. PATENT DOCUMENTS

| | | | |
|---|---|---|---|
| 2,295,504 | * | 9/1942 | Shelton ................... 514/642 |
| 3,169,983 | | 2/1965 | Hunter et al. ............ 260/462 |
| 5,312,841 | * | 5/1994 | Peterson ................. 514/711 |
| 5,438,034 | * | 8/1995 | Walker .................. 504/158 |
| 6,080,789 | * | 6/2000 | Lutz .................... 514/642 |

FOREIGN PATENT DOCUMENTS

| | | |
|---|---|---|
| 650304 | 2/1951 | (GB) . |
| 669506 | 4/1952 | (GB) . |

OTHER PUBLICATIONS

Block, Seymour S. Disinfection, sterilization, and preservation. 4th edition, Lea & Febiger, Philadelphia, pp. 225–252, 1991.*
*Cationic Surfactants*, E. Jungerman Ed., pp. 56–57, Marcel Dekker, Inc., 1969.
Nicholas, "Interaction of Preservatives with Wood," *The Chemistry of Solid Wood,* Advance in Chemistry Series #207, Powell ed., (A.C.S. 1984).
Preston, J.A.O.C.S. 60:567 (1983).
Butcher et al., *Chemical Abstracts* 91:1526267b (1979).
*Industrial Organic Nitrogen Compounds,* Astle Ed. p 66, Reinhold Inc, 1961.
*Organic Reactions,* 11, Chptr. 5, 377, Krieger Publishing Co., 1975.
*Chemical Abstracts* 110:212114e (1989).
*Chemical Abstracts* 114:24824v (1991).

* cited by examiner

*Primary Examiner*—John Pak
(74) *Attorney, Agent, or Firm*—Darby & Darby

(57) ABSTRACT

A method for disinfecting a substrate is provided. The substrate is contacted with a biocidal effective amount of a composition of (a) at least one quaternary ammonium carbonate, bicarbonate, or any combination thereof; (b) a solvent selected from the group consisting of water and propylene glycol; and (c) optionally, a surfactant.

11 Claims, 2 Drawing Sheets

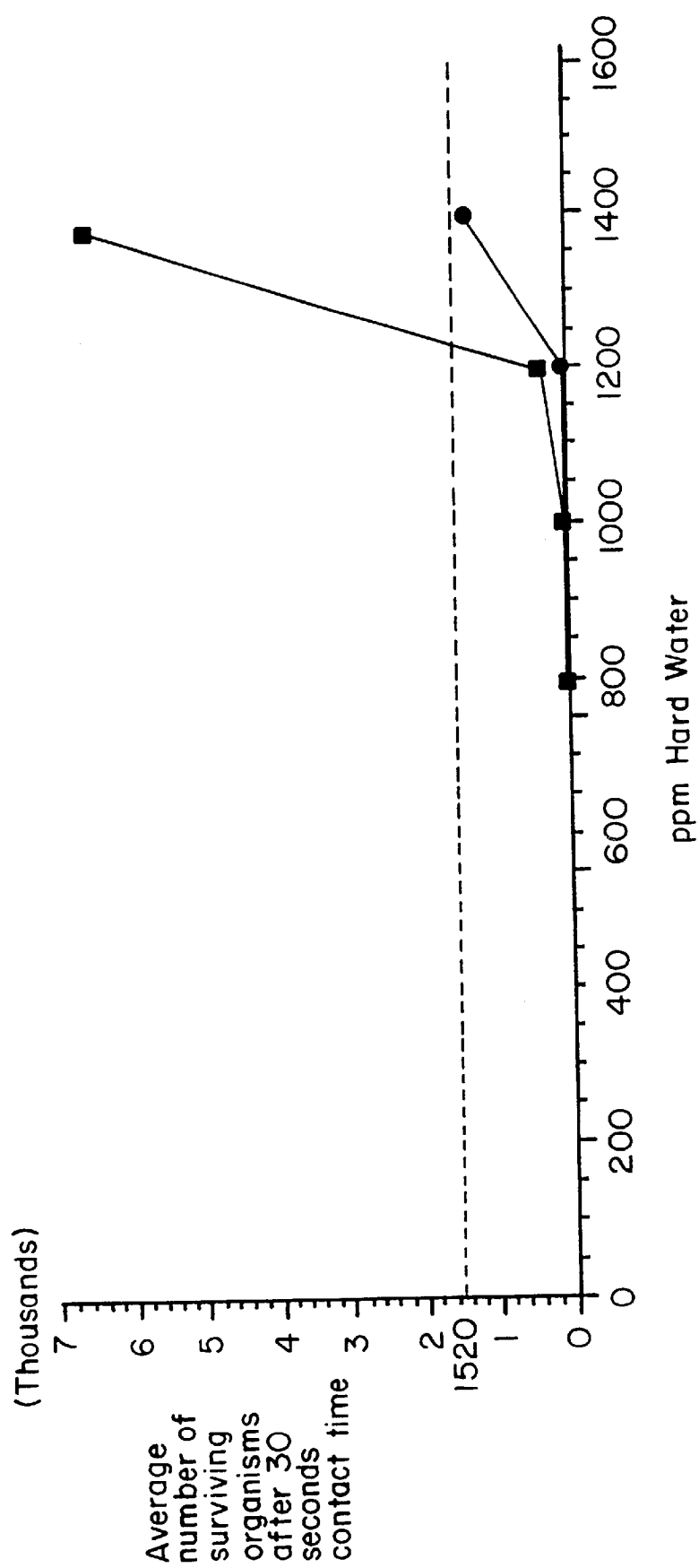

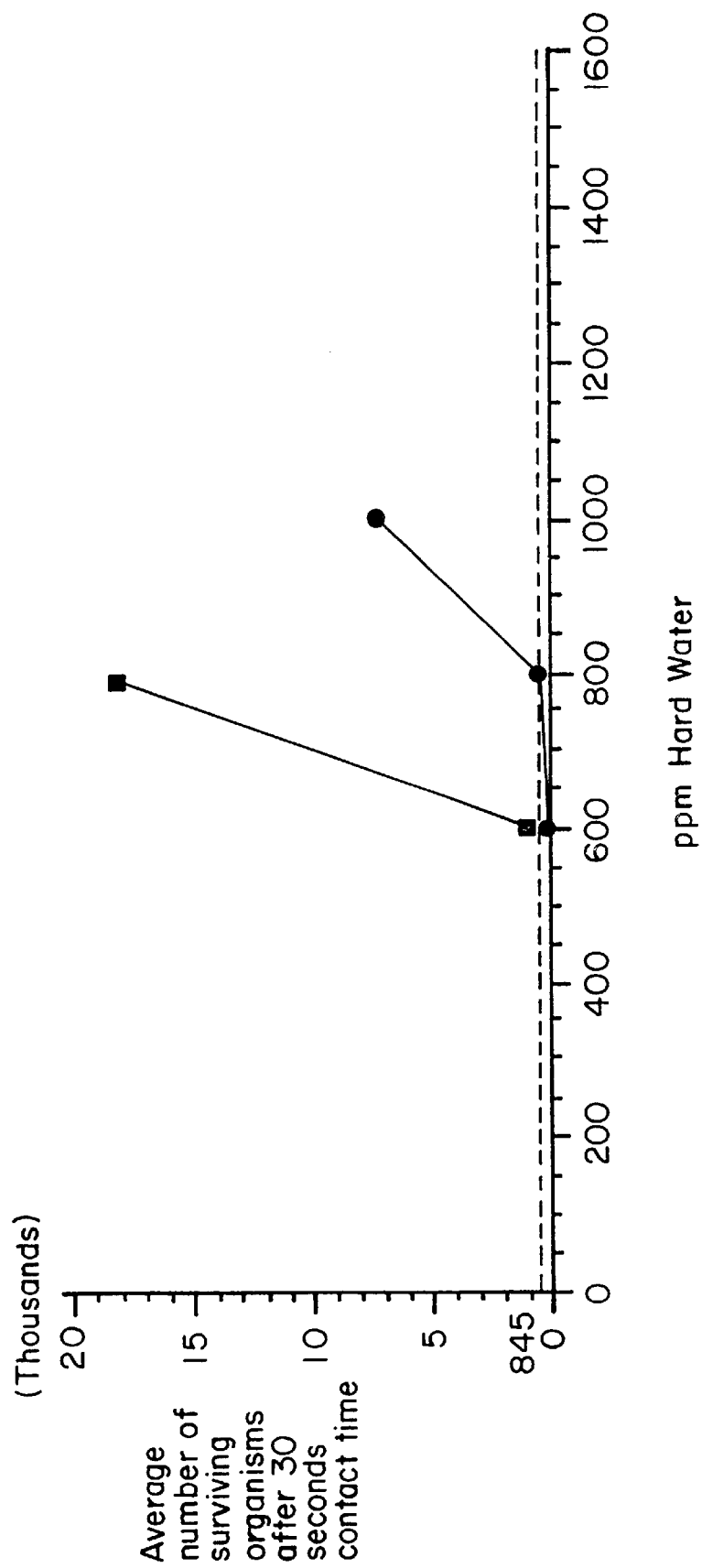

DISINFECTING USE OF QUATERNARY AMMONIUM CARBONATES

This application is a continuation of Ser. No. 08/931,184, filed on Sep. 16, 1997, now U.S. Pat. No. 6,080,789, which is a continuation of Ser. No. 08/352,899, filed on Dec. 9, 1994, now abandoned.

FIELD OF THE INVENTION

This invention relates to the use of quaternary ammonium carbonate compositions as low corrosion disinfectants, particularly in hard water solvents.

BACKGROUND OF THE INVENTION

The biocidal activities of other quaternary ammonium compositions have been reported. The biocidal activities of various quaternary ammonium chlorides against bacteria, fungi, and algae are tabulated in *Cationic Surfactants*, E. Jungerman Ed., pp. 56–57, Marcel Dekker, Inc., 1969. Nicholas, "Interaction of Preservatives with Wood," *Chemistry of Solid Wood*, Advance in Chemistry Series #207, Powell ed., (A.C.S. 1984) notes that didecyldimethyl ammonium compounds, and particularly didecyldimethylammonium chloride, are potential biocides. Preston, J.A.O.C.S. 60:567 (1983) concurs and suggests that maximum fungitoxicity is exhibited with dialkyldimethyl compounds having $C_{10}$–$C_{12}$ alkyl groups. Butcher et al., Chem Abstracts No. 91:152627b, suggests that the presence of an acid or a base can affect the activity of didecyldimethylammonium quats.

Ruseggan, in U.K. Patent Publication No. 650,304, discloses a detergent which includes a tetra alkyl quaternary ammonium halide or hydroxide in which two alkyl groups contain from 6 to 9 carbon atoms in each hydrocarbon group and the other two alkyl groups contain 3 to 9 carbon atoms each together with a weak alkali. Such compositions may also include an alkali substrate (See U.K. Patent Publication No. 669,506).

Hunter et al., U.S. Pat. No. 3,169,983, disclose glycol monoborate salts of quaternary amines that are useful as active biocides and fungicides in soaps, detergents, and dry cleaning compositions.

It has now been discovered that quaternary ammonium carbonates can be used as disinfectants, particularly in hard water. These compositions have low corrosion properties.

Some carbonate quats can be prepared by heating trimethylamine with carbon dioxide and methanol above 200° C. and at 85 to 95 atmospheres. *Industrial Organic Nitrogen Compounds*, Astle Ed. p 66, Reinhold Inc, 1961. However, this reaction is limited to the methyl compound because higher homologs decompose to olefins by the Hoffman elimination reaction. See, *Organic Reactions*, 11, Chptr. 5, 377, Krieger Publishing Co., 1975.

Chem Abst. 110, 212114 (1989) suggests that dimethyl carbonate will react with triethylamine in methanol in twelve hours at 115° C. and under pressure to yield a methyl carbonate quat ester.

Chem Abst. 114, 24824 (1991) discloses that 6-hydroxyhexyldimethylamine reacts with dimethyl carbonate to yield a carbonate ester quat.

BRIEF DESCRIPTION OF THE DRAWINGS

FIG. 1 is a graphic illustration of the sanitizing effect of a composition according to the present invention.

FIG. 2 is a graphic illustration of the sanitizing effect of a composition according to the present invention.

SUMMARY OF THE INVENTION

A method for disinfecting a substrate is provided. The substrate is contacted with a biocidal effective amount of a composition comprising (a) at least one quaternary ammonium carbonate, bicarbonate, or combination thereof; (b) a solvent selected from the group consisting of water and propylene glycol; and (c) optionally, a surfactant.

DETAILED DESCRIPTION OF THE INVENTION

Quaternary ammonium compounds useful in the present invention are quaternary ammonium compounds having carbonate and/or bicarbonate anions. Preferred quaternary ammonium carbonates have the formula

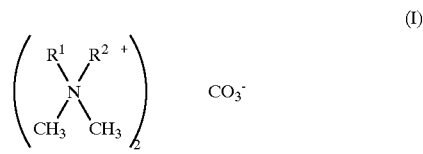

(I)

wherein $R^1$ is a $C_1$–$C_{20}$ alkyl or aryl-substituted alkyl group, or a benzyl group and $R^2$ is a $C_4$–$C_{12}$ alkyl or aryl-substituted alkyl group, or a benzyl group.

A preferred carbonate quat is one in which $R^1$ is a $C_1$–$C_{20}$ alkyl or aryl-substituted alkyl group and $R^2$ is a $C_8$–$C_{20}$ alkyl group. Preferably, $R^1$ and $R^2$ are the same $C_8$–$C_{20}$ alkyl group. A most preferred carbonate quat is didecyldimethylammonium carbonate wherein $R^1$ and $R^2$ are a $C_{10}$ alkyl group and most preferably an n—$C_{10}$ alkyl group. Didecyldimethylammonium carbonate, when observed as a 70–80 percent by weight solution in a 50 percent by weight alcohol/50 percent by weight solvent is a yellow/orange liquid that has a slightly fruity odor. This formulation has a flash point of about 160° F., and it reacts with carboxyl containing compounds.

The stability, and particularly the thermal stability, of carbonate quats is far superior to that of hydroxy quats, making these carbonate quats suitable for concentrating and as stock intermediates for further processing.

One or more of these carbonate quats can be used alone or in combination with the corresponding bicarbonate quat(s). One or more bicarbonate quats can be used alone as well.

Preferred bicarbonate quats have the formula

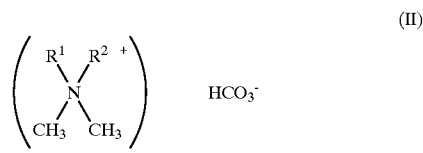

(II)

wherein $R^1$ and $R^2$ are as defined above.

Although certain carbonate quats can be prepared by a variety of methods, an indirect synthesis method that can be used to prepare a variety of quaternary ammonium carbonate compositions, including, but not limited to, quaternary ammonium carbonate compounds, preferably $C_1$–$C_{20}$ alkyl or aryl-substituted alkyl, $C_8$–$C_{20}$ alkyl quaternary ammonium carbonate compounds including, but not limited to, di $C_8$–$C_{12}$ alkyl quaternary ammonium carbonate compounds, and most preferably didecyldimethylammonium carbonate, is preferred.

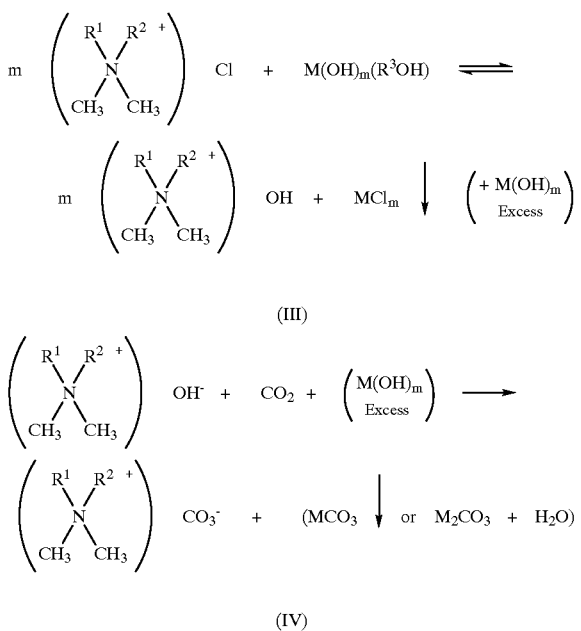

wherein $R^1$ and $R^2$ are as defined above; preferably $R^1$ is a $C_1$–$C_{20}$ alkyl or aryl-substituted alkyl group; $R^2$ is a $C_8$–$C_{20}$ alkyl group; and most preferably $R^1$ is the same as $R^2$ and $R^1$ is a $C_8$–$C_{12}$ alkyl group; $R^3$ is a straight chain $C_1$–$C_4$ alkyl group; M is a mono-, bi-, tri-valent metal, preferably a mono-valent metal, and most preferably an alkali metal; and m is 1 if M is mono-valent, 2 if M is di-valent, and 3 if M is tri-valent.

An appropriate quaternary ammonium chloride with corresponding substituents on the nitrogen atom such as, for example $C_1$–$C_{20}$ alkyl or aryl-substituted alkyl, $C_8$–$C_{20}$ alkyl, and preferably a di $C_8$–$C_{12}$ alkyl, quaternary ammonium chloride is used as a starting material and is reacted with a metal hydroxide to yield a corresponding quaternary ammonium hydroxide intermediate such as, for example $C_1$–$C_{20}$ alkyl or aryl-substituted alkyl, $C_8$–$C_{20}$ alkyl, and preferably a di $C_8$–$C_{12}$ alkyl, quaternary ammonium hydroxide intermediate. The hydroxy quat intermediate(s) and any excess metal hydroxide are then reacted with carbon dioxide to yield the carbonate quat(s) and the metal carbonate.

Many quaternary ammonium chlorides such as, for example di $C_1$–$C_{12}$ alkyl quaternary ammonium chlorides, are suitable reactants to prepare the intermediate hydroxy quat, but didecyldimethylammonium chloride is preferred. The selections of the $R^1$ and $R^2$ substituents of the chloride quat reactant are determinative of the hydroxy quat intermediate, and therefore, of the carbonate quat product.

Special mention is also made of processes wherein $R^1$ is a methyl, $C_8$ alkyl, $C_9$ isoalkyl, $C_{10}$ alkyl, $C_{12}$ alkyl, $C_{14}$ alkyl, $C_{16}$ alkyl, or benzyl group; and $R^2$ is a $C_{10}$ alkyl, $C_{12}$ alkyl, $C_{14}$ alkyl, or $C_{16}$ alkyl group.

The metal hydroxide reactant is a mono-, bi-, or tri-valent metal hydroxide, preferably a mono-valent metal hydroxide, and most preferably an alkali metal hydroxide such as sodium hydroxide or potassium hydroxide. Special mention is made of potassium hydroxide. The metal chloride first step reaction product will precipitate and is easily removed, i.e. by filtration or the like, yielding a hydroxy quat/solvent reaction product. The hydroxy quat can be separated therefrom by drying or the like, if desired.

The first reaction (III) is conducted in a solvent which comprises a $C_1$–$C_4$ normal alcohol. Preferably, the solvent is ethanol, and most preferably, anhydrous ethanol. The reaction to form the hydroxy quat is typically an equilibrium reaction, but the use of a $C_1$–$C_4$ normal alcohol solvent drives the reaction sharply to the hydroxy quat.

The amount of metal hydroxide reactant typically is a stoichiometric amount with respect to the quaternary ammonium chloride reactant. Therefore, on a theoretical basis and if the reaction were complete and unequilibrated, there would be no excess of metal hydroxide reactant upon completion of the intermediate reaction. In practice, yield when using a stoichiometric amount of metal hydroxide reactant will range from about 65% to about 95%, but will vary, dependent, in part, upon the particular metal hydroxide reactant.

Yield of the hydroxy quat can be further improved over conventional methods by utilization of a stoichiometric excess of metal hydroxide ranging from about 2% to about 20% excess. If an excess of metal hydroxide is used yield will be increased to from about 95% to about 99%, again varying as above.

The unreacted metal hydroxide is soluble in the hydroxy quat/solvent intermediate.

Hydroxy quat and any unreacted metal hydroxide are then reacted with at least a stoichiometric equivalent of carbon dioxide to yield the quaternary ammonium-carbonate(s), and if any unreacted metal hydroxide were present, the metal carbonate(s). The conversion of the metal hydroxide to the metal carbonate is the preferred reaction of the two carbonations and will proceed more rapidly. The metal carbonate will precipitate and can be separated easily, i.e. by filtration or the like, leaving the stable carbonate quat(s) or carbonate quat(s)/solvent reaction product.

The carbonation step can also produce the bicarbonate quat or the metal carbonate quat as byproducts. The carbonate quat alone or in combination with the bicarbonate quat is suitable for use in disinfectant compositions of the present invention.

Mixing, adding, and reacting of the components in the present invention can be accomplished by conventional means known to those of ordinary skill in the art. The order of addition of reactants or solvent in any individual step does not affect the process. Reactants and/or solvent can be added sequentially or simultaneously in any suitable reaction vessel. For example, the metal hydroxide may be dissolved in alcohol and the resultant mixture added to the chloride quat or the chloride quat may be dissolved in alcohol and the metal hydroxide added to the resultant mixture. Importantly, the method of the present invention is suitable for commercial scale production techniques and equipment, yet convenient for small scale work.

Typically, the reactants and solvent of the chloride quat to hydroxy quat reaction (III) will be stirred and heated to from about 20° C. to about 70° C. and held at that temperature for a period of from about 1 hour to about 5 hours. The reaction mixture is then cooled, first to room temperature and then to about 0° C. where it is held for about 1 hour to about 2 hours. Any precipitated metal chloride is collected as is known in the art, i.e. such as by filtration.

Alternatively, the first reaction reactants and solvent can be stirred at a slightly elevated temperature, i.e. from about 20° C. to about 40° C., to yield the hydroxy quat/solvent mixture. Hydroxy quat can be separated as above.

The carbon dioxide is generally bubbled for a suitable period known to those of ordinary skill in the art through the hydroxy quat/solvent supernatant after the metal chloride precipitate has been separated. Alternatively, the carbon dioxide can be added as solid dry ice directly to the hydroxy quat. Typically, this time varies from about 0.5 hour to about 1 hour at ambient temperature. Any precipitated metal carbonate is collected as is known in the art, i.e. such as by filtration.

Suitable solvents include water, propylene glycol, or a combination thereof. Carbonate quats display good tolerance to hard water compared with other quats.

Optionally, a surfactant may be added as well. Suitable surfactants include, but are not limited to, non-ionic surfactants, for example, amine oxides, linear alcohol ethoxylate, secondary alcohol ethoxylates, ethoxylate esters, Henkels EPG, betamines, and alkyl polyglycerides.

Other conventional additives such as builders, colorants, perfumes, fragrances, or cleaners may be added as required for application to different substrates.

Suitable substrates include, but are not limited to, hard and soft surfaces, food containers, and skin.

The amount of quaternary ammonium carbonate(s) used to treat a substrate is a biocidal effective amount, i.e. that amount to sanitize or disinfect the substrate. A biocidal effective amount of at least one quat is mixed with a suitable solvent such as water or propylene glycol. The biocidal effective amount will depend upon the use intended and can be determined by one of ordinary skill in the art in light of the present detailed disclosure.

A substrate is considered disinfected or sanitized when 99.999% of the targeted microorganism(s) on or in the substrate are killed.

Typically, the disinfectant composition can either be supplied in a dilutable concentrated form or in a ready to use form. A typical concentrate will comprise from about 19% by weight to about 30% by weight of quat based upon 100% by weight of total composition and a typical ready to use formulation will comprise from about from 10 ppm to about 10,000 ppm of quat based upon total composition.

Treatment of the substrate is accomplished by any means known to those of ordinary skill in the art including, but not limited to, dipping, soaking, brushing, spraying, mopping, washing, or the like. The length of treatment required will vary according to treatment conditions, the selection of which are known to those skilled in the art.

DESCRIPTION OF THE PREFERRED EMBODIMENTS

The following examples illustrate the invention without limitation. All parts and percentages are given by weight unless otherwise indicated.

EXAMPLE 1

Water (86.55%), ethylene diamine tetra acetic acid (EDTA Acid) (Versene 100—Dow Chemical Co.) (0.75%), surfactant (Barlox 12—Lonza, Inc.) (5%), and didecyldimethylammonium carbonate (50% active) (7.7%) were mixed to yield a biocidal composition having a pH of 9.85.

A 20 ml aliquot was frozen overnight in a vial and then was completely thawed at ambient temperature. Results are illustrated in Table 1.

Another 20 ml aliquot was heated at 50° C. for 30 days to evaluate accelerated stability.

Results are illustrated in Table 1.

EXAMPLE 2

Water (84.80%), EDTA Acid (Versene 100) (2.5%), surfactant (Barlox 12—Lonza, Inc.) (5%), and didecyldimethylammonium carbonate (7.7%) were mixed to yield a biocidal composition having a pH of 10.1. Freeze/thaw stability and accelerated stability were determined according to the procedures of Example 1.

Results are illustrated in Table 1.

EXAMPLE 3

Water (86.3%), EDTA Acid (Versene 100) (1%), surfactant (Carsonon N-9—Lonza, Inc.) (5%), and didecyldimethylammonium carbonate (50% active) 7.7% were mixed to yield a biocidal composition having a pH of 9.63. Freeze/thaw stability and accelerated stability were determined according to the procedure of Example 1.

Results are illustrated in Table 1.

TABLE 1

| | Stability | | |
|---|---|---|---|
| Example | 1 | 2 | 3 |
| Freeze/Thaw Stability | No separation No precipitation | No separation Precipitation present | No separation No precipitation No darkening |
| Accelerated Stability | No separation No precipitation No darkening | No separation No precipitation No darkening | No separation No precipitation No darkening |

EXAMPLE 4

*P. aeruginosa* with 5% organic load was dried on stainless steel carriers and then immersed in 600 ppm active of a disinfectant composition prepared according to the method of Example 1 in 400 ppm hard water.

After 10 minutes contact time to the disinfectant, the carriers are aseptically transferred to 10 ml of letheen broth (neutralizer/growth media).

These letheen broth tubes with the carriers are then incubated at 37±1° C. for at least 48 hours. After 48 hours, a cloudy letheen tube indicates growth or failure and a clear tube indicates no goth or pass. Results are illustrated in Table 2. Carrier counts were performed on 10% of the inoculated carriers. Results are illustrated in Table 2.

EXAMPLE 4A

The method of Example 4 was followed, substituting decylisononyldimethylammonium chloride (Bardac 2180—Lonza, Inc.) for the disinfectant composition.

Results are illustrated in Table 2.

EXAMPLE 5

The method of Example 4 was followed, substituting the disinfectant composition prepared according to the method of Example 3.

Results are illustrated in Table 2.

EXAMPLE 6

The method of Example 4 was followed, substituting 600 ppm active of didecyldimethylammonium carbonate (DDA-$CO_3$) for the disinfectant composition.

Results are illustrated in Table 2.

EXAMPLE 7

The method of Example 4 was followed, substituting 700 ppm active of DDA-$CO_3$ for the disinfectant composition.

Results are illustrated in Table 2.

EXAMPLE 8

The method of Example 4 was followed, substituting 800 ppm active of DDA-CO$_3$ for the disinfectant composition. Results are illustrated in Table 2.

TABLE 2

| Example | Disinfecting # Positives/Total | Carrier Counts (10$^6$) |
|---|---|---|
| 4 | 2/60 | 1.30 |
| 4A | 1/20 | 1.14 |
| 5 | 0/60 | 1.34 |
| 6 | 0/60 | 5.7 |
| 7 | 0/20 | 4.6 |
| 8 | 0/20 | 9.0 |

EXAMPLE 9

The method of Example 6 was followed substituting *S. aureus* for *P. aeruqinosa*.
Results are illustrated in Table 3 below.

TABLE 3

| Example | Disinfecting # Positives/Total | Carrier Counts (10$^6$) |
|---|---|---|
| 9 | 0/20 | 3.6 |

EXAMPLE 10

A Ross-Miles pipette (ASTM D1173–53 (reapproved 1940)) was filled with DDA-CO$_3$(1000 ppm active) solution. The solution was run out of the pipette at the top of a clear Ross-Miles receiver. Foam height was read immediately and after 5 minutes by measuring foam production at the top of the foam column at the highest average height to which the rim of the foam has reached. This height is proportional to the volume of air remaining in the foam. The average of two runs is illustrated in Table 4.

COMPARATIVE EXAMPLE 10A

The method of Example 10 was followed substituting Bardac 2180 for the DDA-CO$_3$.
Results are illustrated in Table 4.

EXAMPLE 11

The method of Example 10 was followed substituting decylisononyldimethyl ammonium carbonate for the DDA-CO$_3$.
Results are illustrated in Table 4.

TABLE 4

| | Foam Properties - 25° C. | |
|---|---|---|
| Example | Disinfectant Foam Level (mm) | Foam Level After 5 minutes (mm) |
| 10 | 136 | 126 |
| 10A | 131.5 | 42.5 |
| 11 | 134.5 | 75 |

EXAMPLE 12

19 ml of water containing varying amounts of hard water and containing 150 ppm (active) of DDA-CO$_3$ were inoculated with *E. Coli* (ATCC #1229). After 30 seconds contact time, 1 ml of the inoculated 99 mls was transferred to neutralizer blanks. Then 1.0 ml and 0.1 ml of the 30 seconds neutralizer blanks were plated on to agar to be incubated at 37±1° C. for 48 hours. The plates were then counted to find the number of surviving organisms after 30 seconds contact time. These numbers were compared to the initial numbers count to yield the percent reduction.
Results are illustrated in FIG. 1.

COMPARATIVE EXAMPLE 12A

The method of Example 12 was followed, substituting Bardac 2250 for the DDA-CO$_3$.
Results are illustrated in FIG. 1.

EXAMPLE 13

The method of Example 12 was followed, substituting 100 ppm (active) DDA-CO$_3$ for the DDA-CO$_3$.
Results are illustrated in FIG. 2.

COMPARATIVE EXAMPLE 13A

The method of Example 13 was followed, substituting Bardac 2250 for the DDA-CO$_3$.
Results are illustrated in FIG. 2.

The horizontal axis on FIG. 1 represents the hard water levels (800, 1000, 1100, 1200, and 1400 ppm) and the vertical axis represents the average number of surviving organisms at 30 seconds contact time. In 1400 ppm hard water, the DDA-CO$_3$ average bacterial survival was 1302.5 cfu/plate which is below the highest number of surviving organisms (FIG. 1) that meet the 99.999o kill criteria for the food contact sanitizer test. Bardac 2250 in the same experiment had an average bacterial survival that was 5 times higher, 6597.5 cfu/plate (FIG. 1), which does not meet the 99.9990% kill criteria.

The results of FIG. 2 show that DDA-CO$_3$ at 100 ppm active in 800 ppm hard water meets the 99.999% kill criteria for the sanitizer test with 575 cfu/plate average bacterial survival. Bardac 2250 at 100 ppm active in 800 ppm hard water has 18482.5 cfu/plate average bacterial survival which does not meet the 99.999% kill criteria. These results illustrate the hard water tolerance of the e compositions of the present invention.

EXAMPLE 14

Metal specimens of carbon and alloy steel and an aluminum alloy w ere exposed to didecyldimethylammonium carbonate (46.2% pure). Observations were made after 28 and 90 days, and the amount of weight loss of metal was calculated.

No weight loss w as noted for the aluminum alloy specimens. However, some discoloration was observed and a small portion of the outer surface was pitted, possibly due to oxidation.

The carbon and alloy steel specimens did not exhibit any outward signs of interaction with the carbonate quat. The metal surface was bright and shiny, similar to test initiation. There was a slight rate of corrosion, calculated to be 0.0151 and 0.00630 mils per year for the 28 and 90 day specimens, respectively. It appeared that the corrosion rate decreased with time, as the appearance of the test material from the 28-day and the 90-day exposures did not change significantly.

All patents, applications, articles, publications, and test methods mentioned above are hereby incorporated by reference.

Many variations of the present invention will suggest themselves to those skilled in the art in light of the above detailed description. Such obvious variations are within the full intended scope of the appended claims.

What is claimed is:

1. A method for disinfecting a steel substrate, said method comprising contacting the substrate with a biocidal effective amount of a composition comprising
   (a) at least one quaternary ammonium compound selected from the group consisting of a quaternary ammonium carbonate, a quaternary ammonium bicarbonate, and a combination thereof;
   (b) a solvent selected from the group consisting of propylene glycol, water, and a combination thereof; and
   (c) optionally a surfactant.

2. The method of claim 1, wherein the quaternary ammonium carbonate has the formula

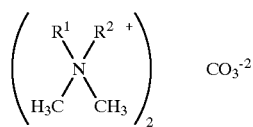

I and the quaternary ammonium bicarbonate has the formula

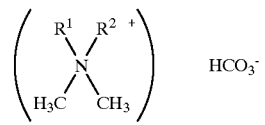

II wherein $R^1$, $R^2$, $R^3$, and $R^4$ independently are a $C_8$–$C_{12}$ alkyl group.

3. The method of claim 2, wherein $R^1$, $R^2_1$ $R^3$, and $R^4$ are the same $C_8$–$C_{12}$ alkyl group.

4. The method of claim 3, wherein $R^1$, $R^2_1$ $R^3$, and $R^4$ are $C_{10}$ alkyl groups.

5. The method of claim 2, wherein $R^1$ and $R^2$ are the same and $R^3$ and $R^4$ are the same.

6. The method of claim 1, wherein the solvent is water.

7. The method of claim 1, wherein the surfactant comprises a non-ionic surfactant.

8. The method of claim 6, wherein said surfactant is selected from the group consisting of amine oxides, linear alcohol ethoxylates, secondary alcohol ethoxylates, ethoxylate ethers, betamines, alkyl polyglycerides, and mixtures thereof.

9. The method of claim 8, wherein the surfactant comprises nonyl phenol ethoxylate.

10. The method of claim 1, wherein the composition further comprises
    (d) a builder,
    (e) a colorant,
    (f) a perfumer,
    (g) a fragrance, or
    (h) a combination thereof.

11. The method of claim 1, wherein the substrate comprises stainless steel.

* * * * *